United States Patent [19]
Barnes et al.

[11] Patent Number: 5,976,839
[45] Date of Patent: Nov. 2, 1999

[54] IMMUNOPOTENTIATION THROUGH COVALENT LINKAGE BETWEEN IMMUNOGEN AND IMMUNOPOTENTIATING MOLECULES

[75] Inventors: Thomas Michael Barnes, Lane Cove; Philip Ralph Lehrbach, Wahroonga; Gregory John Russell-Jones, Middle Cove, all of Australia

[73] Assignee: Bioenterprises PTY Limited, Roseville, Australia

[21] Appl. No.: 08/461,003

[22] Filed: Jun. 5, 1995

Related U.S. Application Data

[62] Division of application No. 07/903,121, Jun. 23, 1992, abandoned, which is a continuation of application No. 07/159,968, Feb. 21, 1987, abandoned.

[30] Foreign Application Priority Data

Mar. 13, 1987 [AU] Australia ................................. PI0846

[51] Int. Cl.$^6$ ........................... C12P 21/06; C12N 15/00; C12N 5/00; C07H 21/04
[52] U.S. Cl. ..................... 435/69.3; 435/320.1; 435/325; 536/23.4; 536/23.7
[58] Field of Search ................................. 435/693, 320.1, 435/325; 536/23.4, 23.7

[56] References Cited

U.S. PATENT DOCUMENTS

| | | |
|---|---|---|
| 4,336,336 | 6/1982 | Silhavy et al. . |
| 4,356,170 | 10/1982 | Jennings et al. . |
| 4,459,286 | 7/1984 | Hilleman et al. . |
| 4,484,923 | 11/1984 | Amkraut et al. . |
| 4,578,269 | 3/1986 | Morein . |

FOREIGN PATENT DOCUMENTS

| | | |
|---|---|---|
| 14506/83 | 11/1983 | Australia . |
| 32423/84 | 3/1985 | Australia . |
| 58943/86 | 1/1987 | Australia . |
| 0 012 078 | 6/1980 | European Pat. Off. . |
| 0 055 942 | 7/1982 | European Pat. Off. . |
| 0 080 806 | 6/1983 | European Pat. Off. . |
| 0 094 797 | 11/1983 | European Pat. Off. . |
| 0 109 688 | 5/1984 | European Pat. Off. . |
| 0 138 644 | 4/1985 | European Pat. Off. . |
| 0 145 359 | 6/1985 | European Pat. Off. . |
| 0 146 416 | 6/1985 | European Pat. Off. . |
| 0 161 188 | 11/1985 | European Pat. Off. . |
| 0 180 564 | 5/1986 | European Pat. Off. . |
| 0 242 243 | 10/1987 | European Pat. Off. . |
| 0 243 333 | 10/1987 | European Pat. Off. . |
| 2 595 374 | 9/1987 | France . |
| 2 004 744 | 4/1979 | United Kingdom . |
| PCT/AU85/0512 | 11/1985 | WIPO . |
| PCT/AU86/0121 | 2/1986 | WIPO . |

OTHER PUBLICATIONS

C. Marcahl et al., *C.R. Acad. Sc. Paris,* vol. 288, Part D, pp. 275–277 (1979).
Freudl et al., *Chem. Abs.* 105(1): 306, ref. No. 3151X and *J. Mol. Biol.* 188(3):491–494 (1986).
Minkley, *Chem. Abs.* 101(3): 158, ref. No. 18263B and *J. Bacteriol.* 158(2):464–473 (1984).
Chatbit et al., *The EMBO Journal* 5(11): 3029–3037, IRL Press Ltd., Oxford, GB (1986).
Melchers et al., *J. Experimental Medicine* 142: 473 (1975).
Bessler et al., *Z. Immun. Forsch* 153: 11 (1977).
Bessler et al., *Z. Immun. Forsch* 155: 387 (1979).
Zollinger et al., *Seminars in Infectious Disease,* vol. 4, Chap. 35, p. 254 (1980).
Bessler et al., *Biochem. Biophys. Research Commun.* 121: 55 (1984).
Jung et al., *Angew. Chem. Int. Ed. Engl.* 24: 872 (1985).
Bessler et al., *Immunobiol.* 170: 239 (1985).
Bessler et al., *J. Immunol.* 135: 1900 (1985).
Vordermeier et al., *Infection and Immunity* 51: 233 (1986).
Bessler et al., *Z. Physiol. Chem. Bd.* 363: 767–770 (1982).
Johnson et al., *Immunobiol.* 165: 27–35 (1983).
Derwent Pat. Abs., Accession No. 86–176377/27, 1986.
Jung et al., *Chem. Abs.* 106(1): 3546a (1987).
Zavala et al., *Science* 228: 1436–1440 (1985).
Lugtenberg, *Chem. Abs.* 105(1): 302, abs. 3099m (1986).
Minkley et al., *Chem. Abs.* 101(21)L 170 abs. 184976f (1984).
Layton et al., *Biol. Abs.* 77(7): 541458 (1984).
Laemmli, *Nature* 227: 680–685 (1970).
Salit et al., *J. Exp. Med.* 151: 716–725 (1980).
Tsai et al., *Anal. Biochem.* 119: 115–119 (1982).
Little et al., *Meth. Immuno. Immunochem.* Academic Press, pp. 128–133 (1967).
Avrameas et al., *Scand. J. Immunol.,* 8(7): 7–23 (1978).
Russell–Jones et al., *J. Exp. Med.* 160: 1476–1484 (1984).
Ogata et al., *J. Bacteriol.* 151(2): 819–827 (1982).
Dyall–Smith et al., *Infectious Diarrhoea in the Young* Elsevier Publishers, pp. 215–220 (1985).
Joyce et al., *Proc. Natl. Acad. Sci. USA* 80: 1830–1834 (1983).

(List continued on next page.)

*Primary Examiner*—Anthony C. Caputa
*Assistant Examiner*—Mark Navarro
*Attorney, Agent, or Firm*—Foley & Lardner

[57] ABSTRACT

A class of carrier molecules which when covalently linked to an immunogen enhances the host's immune response to that immunogen, regardless of whether the complex of carrier and immunogen is administered parenterally, enterally, or orally to the host. Also provided are processes for production of the complexes, as well as hybrid DNA sequences encoding the complexes, recombinant DNA molecules bearing the hybrid DNA sequences, transformed hosts and vaccines comprising the complexes, and methods for production of the vaccine.

18 Claims, 7 Drawing Sheets

OTHER PUBLICATIONS

Mott et al., *Proc. Natl. Acad. Sci. USA* 82: 88–92 (1985).
Wetzler et al., *J. Exp. Med.* 168: 1883–1897 (1988).
Perumal et al., *J. Biol. Chem.* 259: 5357–5360 (1984).
Palva, *FEMS Symp.* 25: 31–37 (1985).
Benz et al., *Crit. Rev. Biochem.* 19: 145–190 (1985).
Makela et al., *Seminars in Infectious Disease IV:* 360–365 (1982).
Riley, *Immunol. Today* 13: 127–130 (1992).
Henning et al., *Eur. J. Biochem.* 136:233–240 (1983).
Perumal et al., *J. Biol. Chem.* 259: 5354–5360 (1984).
Melchers et al., *J. Exp. Med.* 142:473–482 (1975).
Hoffman et al., *Science* 237: 639–642 (1987).
Brown et al., *Vaccine* 12: 102–108 (1994).

FIG. 3a  PLASMID CONSTRUCTIONS

PLASMID CONSTRUCTIONS

IMMUNOPOTENTIATION THROUGH COVALENT LINKAGE BETWEEN IMMUNOGEN AND IMMUNOPOTENTIATING MOLECULES

This application is a divisional application of Ser. No. 07/903,121, filed on Jun. 23, 1992, now abandoned, which is a continuation application of Ser. No. 07/159,968, filed Dec. 21, 1987, now abandoned.

TECHNICAL FIELD

The invention relates to a class of molecules which when linked to an immunogen can enhance the host's immune response to that immunogen regardless of whether the complex is administered parenterally, enterally or orally.

DEPOSITION OF STRAINS

Reference to ATCC 67331, is to an *E. coli* strain deposited with the American Type Culture Collection at 10801 University Boulevard, Manassas, Va. 20110-2209, USA on Mar. 2, 1987.

BACKGROUND ART

In order to protect an animal against an invading pathogen (bacterial, viral or parasite) it is often advisable to vaccinate the animal with the whole organism or with such subunits of the pathogen as to elicit a protective immune response in the host. The immune response generated to such antigenic challenge can often be augmented by the co-administration of an immunopotentiating agent or adjuvant. The best of these agents are the depot type adjuvants (such as Freund's complete adjuvant, Freund's incomplete adjuvant and montanide). These adjuvants are capable of increasing the antibody response after antigen injection to some 50 to 100 times the level obtained with antigen injected alone.

Whilst adjuvants such as Freund's complete adjuvant, Freund's incomplete adjuvant and Montanide can greatly enhance the immune response to an antigen, they suffer from some disadvantages. When used with an antigen in an injectable form, large lesions often form at the site of injection, a situation which renders them unsatisfactory for such use in humans, pets or in meat animals. Furthermore, these adjuvants fail to act as immunopotentiating agents when administered orally or enterally.

DESCRIPTION OF THE INVENTION

This invention relates to a class of molecules which when linked chemically or genetically to an immunogen or hapten can enhance the host's immune response to the immunogen or hapten regardless of whether the complex is administered parenterally, enterally or orally. In addition their use does not result in the formation of large lesions at injection sites.

Molecules which have this activity can be defined as having the general property of being membrane proteins and the examples described herein are from specific types of membrane proteins, more specifically the outer membrane proteins of Gram negative bacteria. Examples cited specifically include the TraT protein, an outer membrane protein of certain strains of *E. coli* which is responsible for the resistance of these strains to killing by serum. Other proteins of this class are the *E. coli* outer membrane proteins OmpA and OmpF. When quantities of TraT, OmpA or OmpF (hereafter called carrier) are injected intramuscularly into mice, without adjuvant, an antibody response is elicited which is comparable to that elicited when a soluble protein such as BSA, flagellin or sheep IgG is mixed with Freund's incomplete adjuvant and then injected. In fact, the antibody response elicited by these outer membrane proteins is so high as to be only marginally increased by adjuvation with Freund's incomplete adjuvant.

It has also been found that oral administration of TraT or OmpA results in the stimulation of significant titres of anti-TraT (1/4096) or anti-OmpA (1/892) serum antibodies.

Similarly it has been found that feeding of moderate quantities ($10^9$–$10^{10}$) of Salmonella or *E. coli* containing TraT in the outer membrane also enhances production of anti-TraT antibodies.

Covalent coupling of a hapten (Dinitrophenol, DNP), peptide (CSP) or a protein (Bovine Serum Albumin, BSA) to OmpA or TraT also acts to enhance the immune response to the DNP, CSP or BSA.

In a first embodiment the invention provides a complex comprising an immunogen coupled to a carrier molecule, such that the carrier molecule causes the immune response of a host to the immunogen to be enhanced when the complex is administered to said host, regardless of whether the complex is administered parenterally, enterally or orally, wherein said immunogen comprises either an antigen or a hapten and said carrier molecule comprises an integral membrane protein of prokaryote or eukaryote origin.

In a preferred embodiment the carrier molecule is an outer membrane protein of a Gram negative bacterium.

Preferably said Gram negative bacterium is *E. coli* or a Salmonella species.

More preferably the carrier molecule is the TraT protein or the outer membrane protein OmpA or OmpF, produced by strains of *E. coli*.

Preferred immunogens of the invention include CSP, the viral capsid protein VP7 from a rotavirus strain, and all or part of the eukaryotic protein minactivin.

The immunogen-carrier complex may be formed by chemical means including: conjugation, for instance, by using either a suitable conjugating or linking agent; and modification and/or reaction of functional groups present on carrier and/or immunogen.

Thus, the invention provides a process for the production of a complex comprising, an immunogen coupled to a carrier molecule, said carrier molecule being an integral membrane protein (imp), of prokaryote or eukaryote origin and said immunogen comprising either an antigen or a hapten, wherein the carrier molecule causes the immune response of a host to the immunogen to be enhanced when the complex is administered to said host, regardless of whether the complex is administered parenterally, enterally or orally, which process comprises one or more of the following steps:

a) reacting the immunogen with the carrier to form said complex;

b) chemically modifying the immunogen to provide at least one functional group capable of forming a chemical linkage, and reacting the modified immunogen and carrier to form said complex;

c) chemically modifying the carrier to provide at least one functional group capable of forming a chemical linkage and reacting the immunogen and modified carrier to form said complex;

d) chemically modifying the immunogen and the carrier to provide functional groups capable of forming a chemical linkage, and reacting the modified immunogen and modified carrier to form said complex;

e) reacting the immunogen with at least one linking agent and reacting the linked immunogen and the carrier molecule to form said complex;

f) reacting the carrier with at least one linking agent and reacting the immunogen and linked carrier to form said complex;

g) reacting the immunogen and carrier with at least one linking agent and reacting the linked immunogen and linked carrier to form said complex.

A preferred process of the invention comprises:

(i) chemically modifying an immunogen to provide at least one functional group capable of forming a chemical linkage; and (ii) reacting the modified immunogen and the carrier to form said complex.

The linking agent may contain a disulfide bond or be cleavable by acid, base or periodate. Examples of such linking agents include N-(4-azidophenylthio)phthalimide, 4,4'-dithiobisphenylazide, dithiobis-(succinimidylpropionate), dimethyl-3,3'-dithiobispropionimidate.2HCl, 3,3'-dithiobis-(sulfosuccinimidylpropionate), ethyl-4-aziodophenyl-1,4-dithiobutyrimidate,HCl, N-succinimidyl-(4-azidophenyl)-1, 3'-dithiopropionate, sulfosuccinimidyl-2-(m-azido-o-nitrobenzamido)-ethyl-1,3'-dithiopropionate, sulfosuccinimidyl-2-(p-azidosalicylamido)-ethyl-1,3'-dithiopropionate, N-succinimidyl-3-(2-pyridyldithio) propionate, sulfosuccinimidyl-(4-azidophenylthio)-propionate, and 2-iminothiolane. Preferred cross-linking agents are disuccinimidyl tartrate and bis-[2-(succinimidyloxycarbonyloxy)-ethyl]sulfone.

Suitably, linking of the carrier and immunogen may be achieved by coupling the carrier to suitable groups of the immunogen.

Where the immunogen-carrier complex is formed by chemical conjugation, for instance, by using either a suitable conjugating or linking agent, preferred conjugating or linking agents include 1-ethyl-3-(3-dimethyl-aminopropyl) carbodiimide, glutaraldehyde, m-Maleimido benzoic acid n-hydroxysuccinimide ester, or N, N$_1$ Dicychohexyl carbodiimide.

The linkage between the immunogen and the carrier molecule may also be made by the preparation of a hybrid protein molecule, such as is produced by recombinant DNA techniques by the insertion into, or addition to, the DNA sequence coding for the carrier, of DNA coding for the immunogen.

Hence, the invention provides a process for the preparation of said complex of carrier molecule with immunogen, which process comprises preparing a hybrid protein molecule. In a preferred process the hybrid protein molecule is produced by recombinant DNA techniques, by the insertion into, or the addition to, the DNA sequence coding for the carrier, of DNA coding for the immunogen.

The invention also provides a hybrid DNA sequence which consists of: a first DNA sequence comprising a DNA sequence which acts as a coding sequence for at least part of an integral membrane protein of prokaryote or eukaryote origin fused to a DNA sequence coding for the amino acid sequence of an immunogen; or a second DNA sequence which hybridizes to said first DNA sequence, from whatever source obtained, including natural, synthetic and semi-synthetic sources; a DNA sequence related by mutation, including single or multiple base substitutions, deletions, insertions and inversions to said first DNA sequence; or a DNA sequence comprising sequences of codons which, on expression, code for a polypeptide displaying similar immunological or biological activity to a polypeptide coded for on expression of the codons of any of the foregoing hybrid DNA sequences and inserts.

Preferred hybrid DNA sequences of the invention code for at least part of TraT, OmpF or OmpA, linked to a DNA sequence coding for the amino acid sequence of an immunogen such that the resulting TraT-(OmpF or OmpA) hybrid proteins are exported to and exposed on the host cell surface.

The invention also provides a fused gene comprising a hybrid DNA sequence of the invention fused to a portable promoter. A preferred promoter according to the invention, is the P$_L$ promoter of the bacteriophage lambda.

Further, the invention provides, a recombinant DNA molecule which comprises a hybrid DNA sequence according to the invention and vector DNA, wherein the vector DNA is plasmid, bacteriophage, viral or cosmid DNA.

A preferred recombinant DNA molecule of the invention includes an expression control sequence operatively linked to the hybrid DNA sequence.

Particularly preferred recombinant DNA molecules according to the invention include: pBTA371, pBTA439, pBTA449, pBTA450 and pBTA586.

Within the scope of the invention is a process for the manufacture of a recombinant DNA molecule which process comprises:

introducing into a cloning vehicle, a hybrid DNA sequence according to the invention.

Preferably the process also includes the step of introducing an expression control sequence into the cloning vehicle.

The invention also provides a host transformed with at least one recombinant DNA molecule according to the invention.

Suitable hosts include E. coli and Salmonella sp.

A preferred transformant is ATCC 67331 (also designated CCTCC 87026).

Also included within the scope of the invention is a process for transforming a host, which process comprises the step of: introducing into a host a recombinant DNA molecule according to the invention.

In a further embodiment the invention provides the complex of carrier with immunogen adapted for parenteral injection into a host or adapted for oral or enteral administration, to elicit both a humoral and mucosal antibody response.

Included within the scope of the invention is a process for the preparation of the complex of carrier with immunogen in a form adapted for parenteral, enteral or oral administration to a host which process comprises preparing the complex and adding it to a pharmaceutically acceptable diluent.

Preferably the invention provides a whole bacterial cell vaccine comprising a hybrid protein according to the invention is exposed on the bacterial cell surface for presentation to the immune system. The whole cell vaccine may be a live or killed whole cell oral vaccine. Alternatively the hybrid protein can be purified from the cell membrane or cellular contents and used as a subunit vaccine administered parenterally, enterally or orally.

The invention also provides a process for the manufacture of a microorganism with the genetic information for the biosynthesis of a hybrid protein comprising at least an immunogen and a carrier comprising at least part of an imp of prokaryote or eukaryote origin, such that the resulting hybrid peptide is exposed on the host cell surface which process comprises culturing a microorganism carrying the necessary genetic information. Where the microorganism is used to provide a subunit vaccine, the process additionally comprises purifying the hybrid peptide from the cell membrane or cellular contents.

BRIEF DESCRIPTION OF THE DRAWINGS

and BSA (FIG. 1b) alone or in combination with various adjuvants. TraT and BSA were mixed with F.I.A. (∆—∆); Montanide 888 (●—●), Alhydrogel (□—□); saline (X—X) FIGS. 1a+1b. A comparison of the antibody response generated to TraT (X—X) OmpA (■—■) and OmpF (○—○) injected in saline is presented in FIG. 1c.

Abbreviations (FIGS. 3 and 4): Resistance to; ampicillin, Ap$^r$; chloramphenicol, Cm$^r$; mercuric chloride, Hg$^+$; tetracycline, Tc; VP7 structural gene, VP7; TraT structural gene, TraT,; TraT VP7 gene fusion, TraT-VP7; lambda bacteriophage P$_L$ promoter region, P$_L$.Restriction endonucleases, Al, AluI; A, AvaI; D, DraI B, BamHI; E, EcoRI; N, NdeI; Pv, PvuII; RV, EcoRV; Ss SspI.

BEST MODE OF CARRYING OUT THE INVENTION

The following examples illustrate preferred embodiments of the present invention, and are in no way limiting on the scope of the invention.

EXAMPLE 1

Isolation of TraT, OmpA and OmpF

E. coli (Strain BTA 1352 containing the plasmid pBTA439) were grown in a fermenter at 30° C. In MEB medium. Cells were harvested following 2 hours of heat induction of TraT at 42° C. Bacteria were concentrated to 2 liters using a 0.1µ hollow fibre cartridge in a Amicon DCIOLA concentrator. The cells were then washed with 10 liters of distilled water and reconcentrated to 800 ml. The bacterial slurry was then removed from the concentrate and the outer membrane proteins (TraT, OmpA and OmpF) extracted from the cells by the addition of 200 ml of 1 M sodium acetate buffer pH 2.5, followed by 1 liter of 10% cetrimide (Sigma) in 40% ETOH plus 1 M Ca Cl$_2$. The extraction was allowed to proceed overnight at room temperature, (RT) after which the bacteria were removed by centrifugation (17,000×g, 20 min).

TraT and OmpF were precipitated from the supernatant by the addition of ethanol to 50% and centrifugation (40000×g, 10 min). OmpA was then precipitated from the final supernatant by addition of ethanol to 80%.

Ion Exchange Chromatography

The 50% ethanol pellet containing OmpF and TraT was resuspended in 20 mM Na acetate buffer pH 5.0 containing 0.5% Zwittergent, and loaded onto a 5×50 cm column of DEAE Sepharose (Pharmacia Fine Chemicals) previously equilibrated with 20 mM Na Acetate buffer pH 5.0 containing 0.1% Zwittergent. TraT was found in the column flow through, and bound OmpF was eluted from the column using a linear gradient of 0–1.0M NaCl in equilibration buffer. Fractions were analysed by SDS-PAGE using a modification of the method of Laemmli (Laemmli, U.K. NATURE (LOND) 227:680 1970; Salit et al., J. Exp. Med. 151:716. 1980) and fractions containing isolated TraT or OmpF were pooled and concentrated by ethanol precipitation.

Sephacryl S-300 chromatography

The 80% ethanol pellet containing OmpA was resuspended in 1% SDS in 20 mM Tris. HCl.pH 8.8. Fractions were collected, analysed by SDS-PAGE and fractions containing OmpA were pooled and concentrated by ethanol precipitation.

Proteins purified by the above methods were found to be free of LPS when examined by SDS-PAGE and silver stained by the method of Tsai C. M. and Frasch, C. E. Anal. Biochem 119:115. (1982).

Dinitrophenylation of Carriers

TraT, OmpA and OmpF were dintrophenylated according to the method of Little and Eisen "Methods in Immunology and Immunochemistry" (E. D. Williams, CA and Chase, M. W.) 1, p. 128 Academic Press, N.Y. (1967). Briefly, carriers (in 0.1M carb/bicarb buffer pH 9.5) were reacted with a 0.1M solution of DNFB (in Acetone) overnight at RT. The proteins were then dialysed extensively against the coupling buffer.

Glutaraldehyde coupling

Bovine serum albumin (BSA) (from Sigma Chemical Co. St. Louis, Miss.) was coupled to TraT, OmpA and OmpF using the two step glutaraldehyde procedure of Avrameus et al (1978). Briefly, BSA was reacted with 0.2% glutaraldehyde for 2 hrs at R.T. The protein was then dialysed overnight against carb/bicarb buffer pH 9.5 followed by the addition of omp's at a molar ratio's of 1:1 BSA:omp and reacted for 24 hrs at RT. Finally ethanolamine (Sigma) was added to a final concentration of 0.1M, (1 hr, RT) followed by overnight dialysis at 4C against 0.1M carb/bicarb buffer pH 9.5.

ANTIGEN ADMINISTRATION

1. Rabbits

New Zealand white rabbits (2–2.5 kg) were injected intramuscularly with antigen in 0.5 ml of sterile physiological saline.

Injections were performed on days 0 and 36. Weekly bleedings were obtained from the longitudinal vein in the rabbits ear and antibody titres were measured by a standard ELISA using TraT, OmpA, BSA or DNP-sheep IgG as coating antigens.

2. Mice

Female C57BL/6J mice (18–22 gm) were obtained from the Animal Resources Centre (Perth, Western Australia). All mice were starved for 3–4 hours prior to oral or intramuscular (i.m.) administration of antigens. Mice were fed antigen at appropriate concentrations in 0.5 ml of 0.1M carb/bicarbonate buffer pH 9.5 using a specially prepared feeding needle. Parallel doses of antigen were injected i.m., in 0.1 ml of sterile physiological saline, into the left hind leg. Groups of 5 mice receiving antigen either orally or im were given two identical doses of antigen, on day 0 and day 14. A blood sample was taken (approx. 0.5 ml) from the retro-orbital plexus on day 14 and day 21. Mice were then sacrificed by cervical dislocation and gut washes performed on the small intestine in the following manner. The small intestine was carefully removed and a small quantity of washing buffer (1.0 ml, 30 mM Tris.HCl pH 8.8, 0.9% NaCl, 50 mM EDTA plus 1.0% Tween 20) introduced into the lumen of the gut via a blunt ended feeding needle. After gently kneading the intestine and contents were squeezed out through forefinger and thumb. Gut washes so obtained were immediately centrifuged to remove debris and stored at −20° C. until assayed. Blood samples were allowed to clot at 4° C. before removal of the serum and storage at −20° C.

Enzyme Linked Immunosorbent Assay (ELISA)

The ELISA for the determination of antibody titres was perfomed as described previously by Russell-Jones et al. J. Exp. Med 160:1467, (1984). Titres are expressed as the reciprocal of the antiserum dilution, which gave a ELISA reading of 0.5 after 45 mins at 37° C.

EXAMPLE 2

Effect of adjuvant on the antibody response to integral membrane proteins

The potential of imps to act as self adjuvanting molecules when injected i.m. was examined. The antibody titre generated when TraT FIG. (1a, X—X) or BSA FIG. (1b X—X) were injected alone was compared to that generated when TraT (FIG. 1a) or BSA (FIG. 1b) were mixed with a number of adjuvants.

Figure 1A:
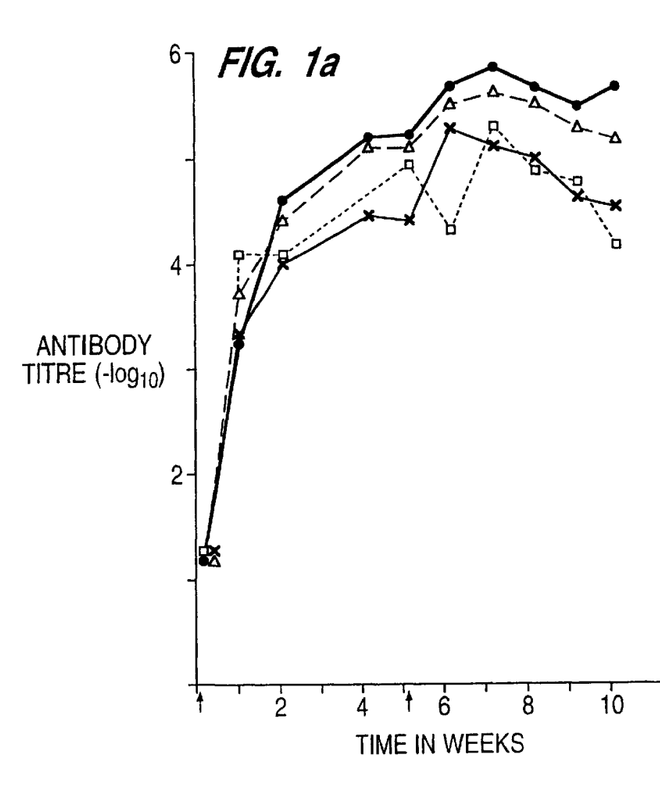
FIGS. 1A–1C Modifications of the immune response by adjuvants. Rabbits were injected i.m. with TraT, (FIG. 1a)
Figure 1B:
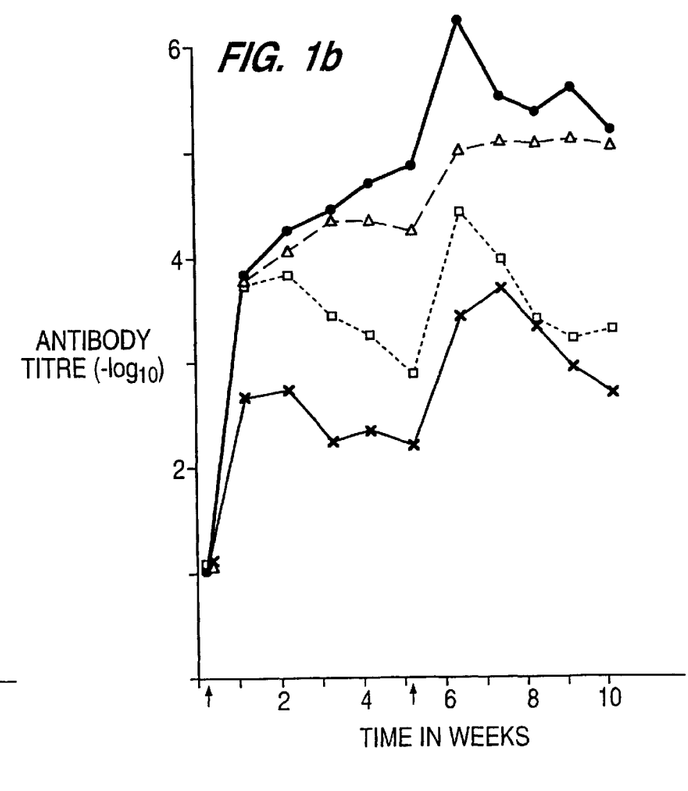

Intramuscular administration of TraT, in saline quickly elicited high titres of serum antibody to the immunizing agent (FIG. 1a). In fact the titres generated by TraT in saline could only be increased by a factor of 4–8 fold by injection of this antigen in adjuvants such as montanide or FIA (FIG. 1a). This is in direct contrast to the response generated by the soluble antigen BSA. In this case a poor antibody response was generated to the antigens administered in saline, but was markedly increased 60–100 fold by injection of the antigen in FIA or montanide (FIG. 1b).

Figure 1C:
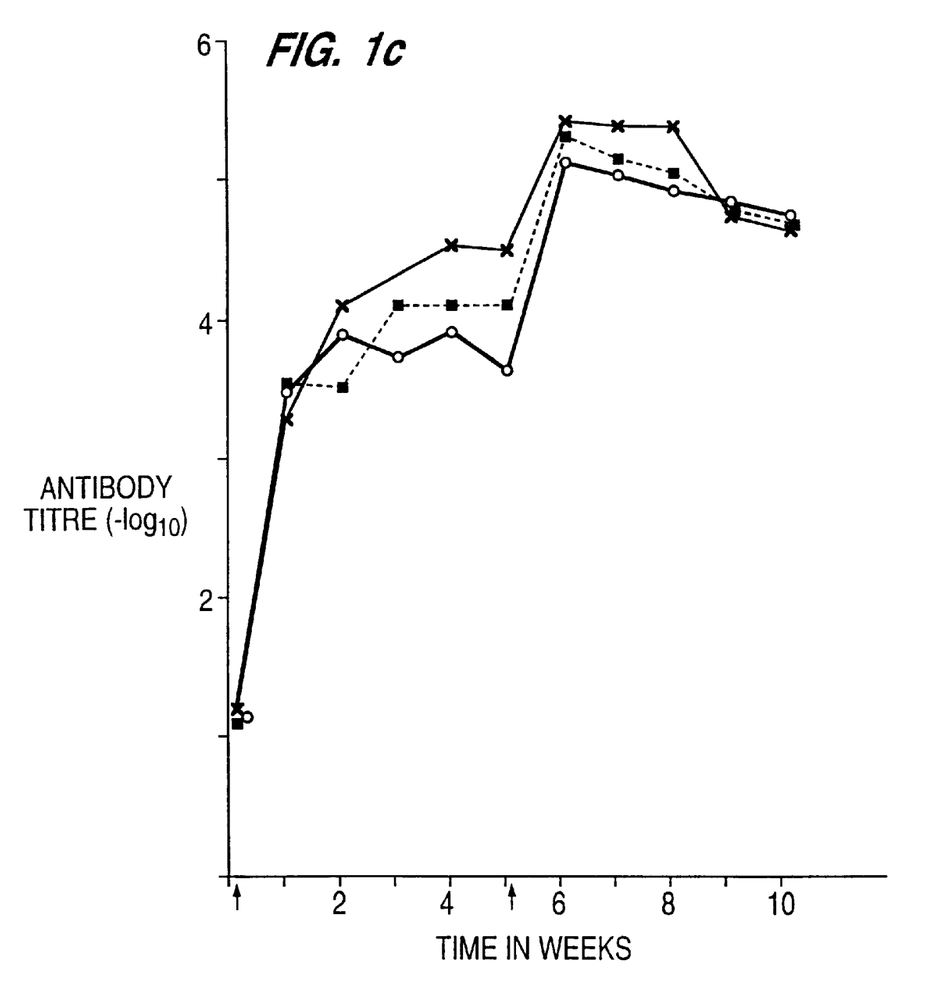

Similarly injection of OmpA and OmpF in saline alone also elicited high serum Ab titres. In fact, surprisingly similar antibody titres were elicited by injection of 100 μg TraT, OmpA or OmpF (FIG. 1c).

EXAMPLE 3

Examination of the adjuvanting ability of immunogen—imp complexes

TraT and OmpA were examined for their ability to augment anti-hapten (DNP) and anti-protein (BSA) responses. The two imps were substituted with DNP using dinitrofluorobenzene (see Example 1) or were glutaraldehyde cross-linked to BSA (see Example 1) and then injected i.m.

Figure 2A:
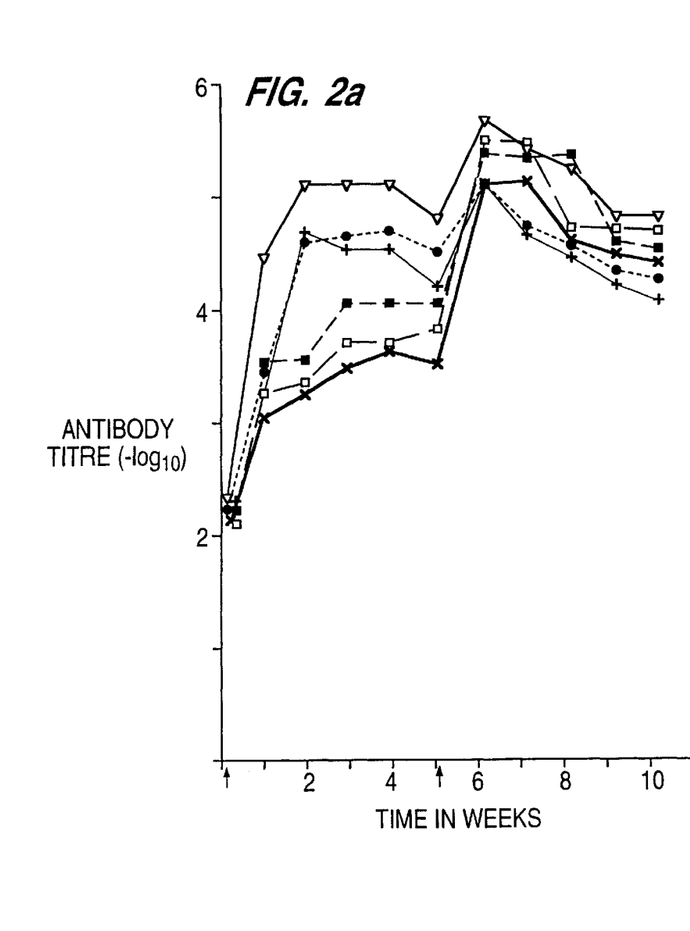
FIGS. 2A–2D Stimulation of the antibody response to DNP and BSA by coupling to TraT and OmpA. Dinitrophenylated preparations of TraT (+—+), Omp A (X—X) and BSA (▼—▼) were compared for their ability to stimulate anti-carrier (FIG. 2a) and anti-DNP antibody responses (FIG. 2b) following im injection. The antibody response to TraT (●—●) and Omp A (■—■) injected alone was also determined. Similarly BSA was injected in saline (○—○), mixed in FIA (▼—▼) or covalently conjugated to TraT (▽—▽) or Omp A (□—□) and the anti-BSA response was determined (FIG. 2c). The anti-TraT and anti-Omp A responses to these congugates are shown in FIG. 2a. The immunopotentiating activity of imps was examined when BSA was injected covalently linked to TraT (▽—▽) or Omp A (□—□), when it was mixed with TraT (▲—▲) or Omp A (■—■) or when it was injected at a separate site from TraT (∆—∆) or Omp A (●—●) (FIG. 2d).
Figure 2B:
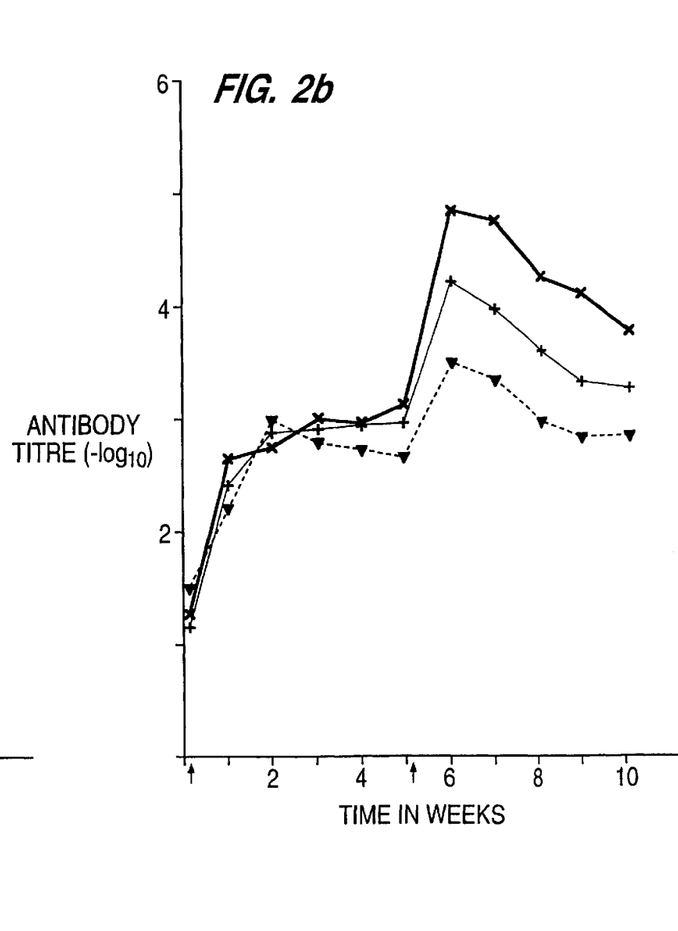
Figure 2C:
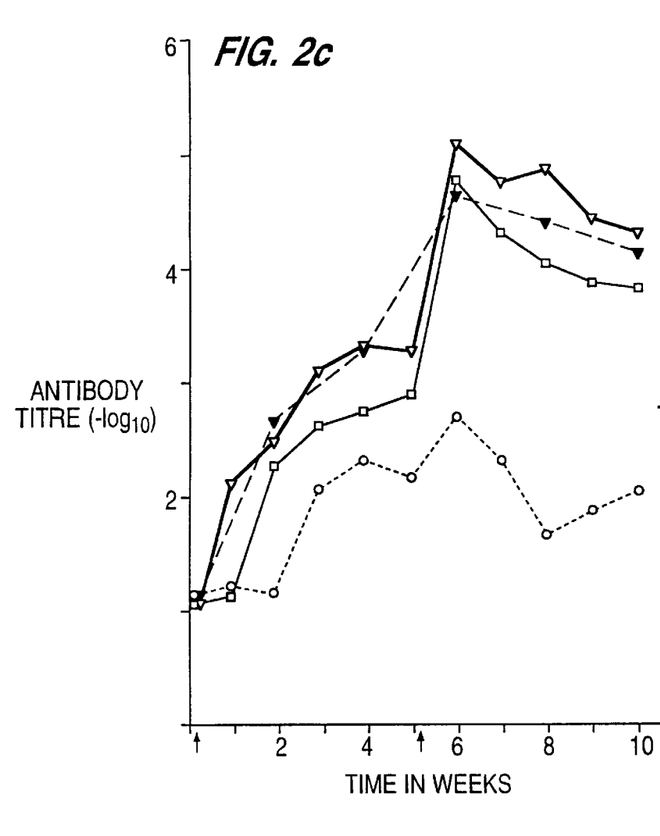
Figure 2D:
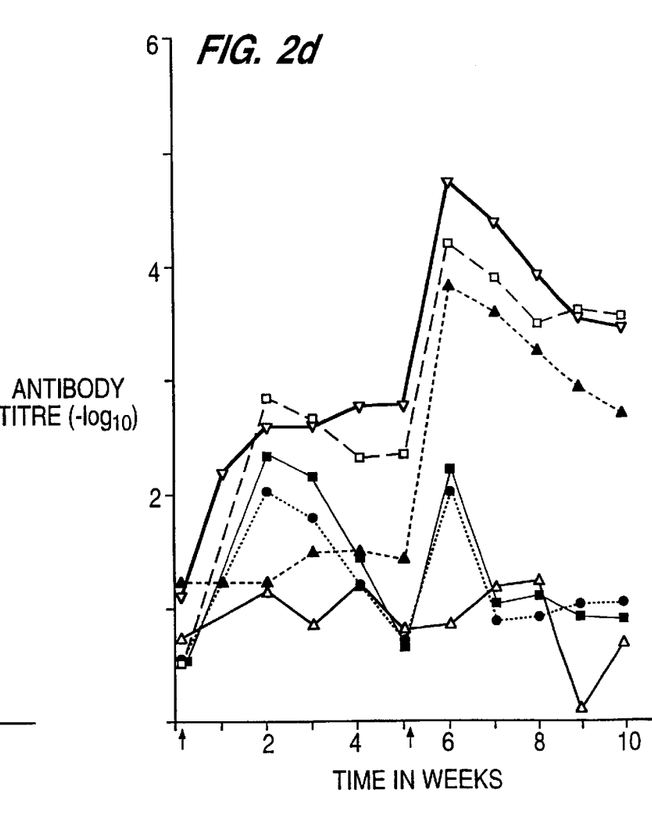

Coupling of DNP or BSA to either TraT or OmpA had little effect on the generation of an anti-imp response (FIG. 2a, cf 1c). Dinitrophenylation of the imps did however increase the anti-DNP response some four to sixteen fold higher than the response seen to DNP-BSA when it was injected in saline (FIG. 2b). Similarly the anti-BSA response was greatly enhanced when BSA was administered in FIA (FIG. 2c). The immunopotentiating effect of TraT or OmpA on the anti-BSA response was greatest when BSA was covalently linked to the imps. In fact injection of BSA at a separate site from the imp actually depressed the secondary response to BSA (cf 2d and 2c).

EXAMPLE 4

Effect of Dose on the immune response to TraT

The effect of increasing dose of TraT administered either i.m. or per os. was examined in mice.

Groups of 5 mice were immunized by intramuscular injection or oral feeding with increasing doses of TraT. Mice received doses on day 0 and day 14. On day 21 mice were bled, sacrificed and gut washes obtained. Antibody titres were increased by ELISA.

As can be seen from Table 1 increasing doses of TraT administered orally or parenterally led to a dose dependent increase in serum anti-TraT Ab response.

Parenteral administration was however much more effective than oral administration.

TABLE 1

| Dose of antigen | Route of administration | | | | | | |
|---|---|---|---|---|---|---|---|
| | Intramuscular | | per os | | | | |
| | serum | IgG | serum | IgG | Gut | IgA | Gut IgA |
| 0.1 | 2,048 ± 900 | — | — | | 6 ± 2 | | 7 ± 4 |
| 1 | 3,565 ± 1,300 | 7 ± 2.6 | 9 ± 3 | | | | 6 ± 2 |
| 2 | 10,809 ± 1,900 | 2 ± 2 | 13 ± 5 | | | | 56 ± 8 |
| 5 | 5,405 ± 400 | 13.9 ± 9 | 24 ± 3 | | | | 42 ± 7 |
| 10 | 28,526 ± 7,280 | 12.0 ± 2 | 16 ± 4 | | | | 18 ± 5 |
| 25 | 24,833 ± 6,040 | 9.1 ± 3 | 6 ± 2 | | | | 7 ± 4 |
| 50 | 49,667 ± 3,020 | 97 ± 25 | 9 ± 5 | | | | 11 ± 6 |
| 100 | 65,536 ± 16,000 | 64 ± 36 | — | | | | — |
| 200 | 150,562 ± 64,000 | 675 ± 400 | 32 ± 20 | | | | 14 ± 7 |
| 400 | 86,475 ± 19,000 | 97 ± 45 | 6 ± 2 | | | | 24 ± 13 |

EXAMPLE 5

Examination of the hapten density on the ability of the imps to act as carriers for an anti-DNP response TraT, OmpA and OmpF were substituted with different ratios of DNP:imp as described in Example 1. Groups of 5 mice were injected i.m with 50 μg doses of the DNP: carrier complex on days 0 and 14. On day 21 mice were bled and the Ab titres determined by ELISA.

Increasing the substitution ratio of DNP to carrier from 0.5:1 to 4:1 increased the anti-hapten response considerably. Substitutions of greater than 10:1 appeared to decrease the anti-hapten response.

TABLE 2

| Antigen | Substitution | Route | Antibody response (serum IgG) |
|---|---|---|---|
| DNP TraT | 0.5:1 | i.m | 21 ± 13 |
| | 1:1 | i.m | 337 ± 71 |
| | 2:1 | i.m | 1552 ± 536 |
| | 4:1 | i.m | 3104 ± 954 |
| DNP-ompA | 0.5:1 | i.m | — |
| | 1:1 | i.m | 84 ± 20 |
| | 2:1 | i.m | 256 ± 109 |
| | 4:1 | i.m | 776 ± 164 |
| DNP - omp F | 0.5:1 | i.m | 7 ± 4 |
| | 1:1 | i.m | 49 ± 12 |
| | 2:1 | i.m | 97 ± 28 |
| | 4:1 | i.m | 337 ± 115 |

EXAMPLE 6

Generation of an anti-CSP response by coupling to TraT

A synthetic peptide derived from the circumsporozoite protein (CSP) antigen of P. falciparum of the following sequence: $NH_2$ Cys (Asn Pro Asn Ala)$_4$, was synthesized and used to conjugate to TraT in order to examine the adjuvating effect of TraT for the peptide antigen.

The CSP antigen was coupled to Tra T using either glutaraldehyde or maleimidobenzoic acid n-hydroxy succinimide ester (MBS). Conjugates prepared in this way were injected into a) rabbits on day 0, day 28, which were then bled on day 38, or b) groups of 5 mice on day 0 and 14. Mice were then bled on day 21. Antibody titres were determined as described previously.

Immunization of rabbits or mice with the CSP antigen coupled to TraT using either glutaraldehyde or MBS, resulted in the stimulation of an anti-CSP response which was comparable to that seen when the antigen was coupled to BSA and injected in montanide.

TABLE 3

| Antigen (serum) | Coupling procedure | Animal | Dose ($\mu$g) | Antibody anti TraT | Response anti CSP |
|---|---|---|---|---|---|
| CSP-TraT | glutaraldehyde | rabbit | 200 | 28,526 | 147 |
| CSP-TraT | MBS | rabbit | 200 | 12,417 | 1,024 |
| CSP + montanide | — | rabbit | 200 | 28 | — |
| CSP-BSA + montanide | glutaraldehyde | rabbit | 200 | — | 2,353 |
| CSP-TraT | glutaraldehyde | mouse | 50 | 228,209 | 32 |
| CSP – TraT | MBS | mouse | 50 | 3,566 | 128 |
| CSP ± montanide | — | mouse | 50 | — | — |
| CSP-BSA + montanide | glutaraldehyde | mouse | 50 | — | 9 |

EXAMPLE 7
Genetic construction of a TraT-immunogen protein complex

Figure 3A:
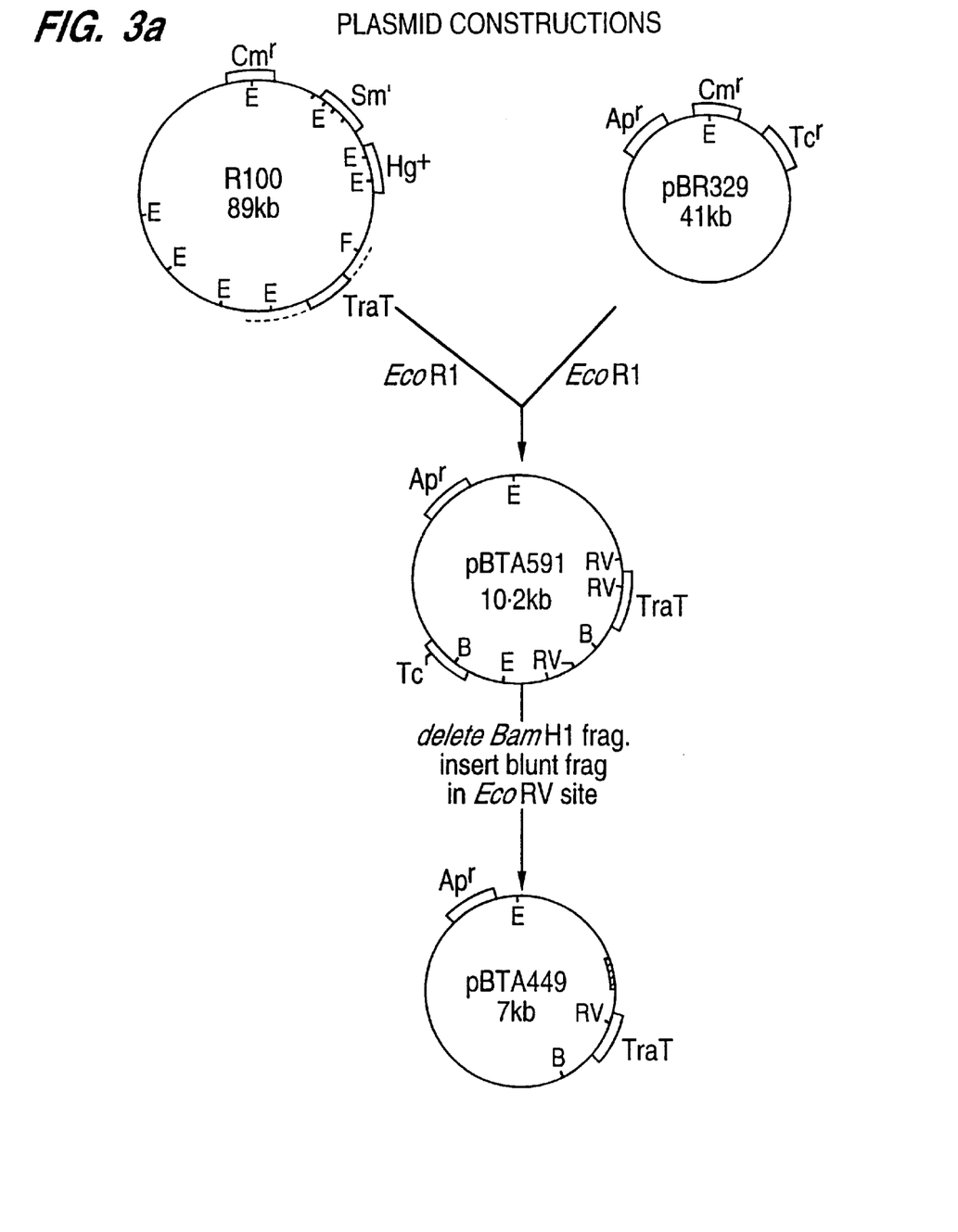
FIG. 3a shows construction of the plasmid pBTA449.

The gene coding for the TraT protein is located on the R plasmid R100 (or R6-5) and the nucleotide sequence of this gene has been determined (Ogata et al, J. Bacteriol 151: 819–827). TraT is an oligomeric lipoprotein situated in the outer membrane which is simultaneously exposed at the cell surface and associated with peptidoglycan, an internal structure. Using these facts a plasmid vector was constructed (FIG. 3a) by initially cloning a 6.0 kb EcoRI fragment of the R100 plasmid which contains TraT into the multicopy plasmid pBR329. Further deletion of an unwanted 3 kb BamHI fragment and inactivation, by insertion of a small blunted ended HaeIII fragment of M13mp8, in an EcoRV site produced pBTA449. This vector plasmid contains the natural TraT promoter which directs the synthesis of TraT. The expression of TraT (or TraT-hybrid proteins subsequently constructed) can be boosted by the replacement of the weak TraT natural promoter with the strong lambda bacteriophage $P_L$ promoter (e.g. in plasmid pBTA439 FIG. 3b or pBTA586 FIG. 4). The TraT gene contains an EcoRV site (unique to pBTA449) where foreign DNA sequences may be inserted such that fusions between TraT and the encoded foreign protein are exported correctly to the cell surface and result in exposure of the foreign protein segment at the cell surface.

In one example the gene for a viral capsid protein (VP7) was used to form TraT-VP7 hybrid proteins. VP7 is a structural protein of rotavirus and antibodies raised against purified VP7 protein effectively neutralize viral infectivity in cell culture (Dyall-Smith et al 1985 In Infectious Diarrhoea in the young ed. S. Tzipori). Thus the VP7 protein, in an appropriately expressed form, is a prime candidate for inclusion in a rotavirus vaccine.

Figure 3B:
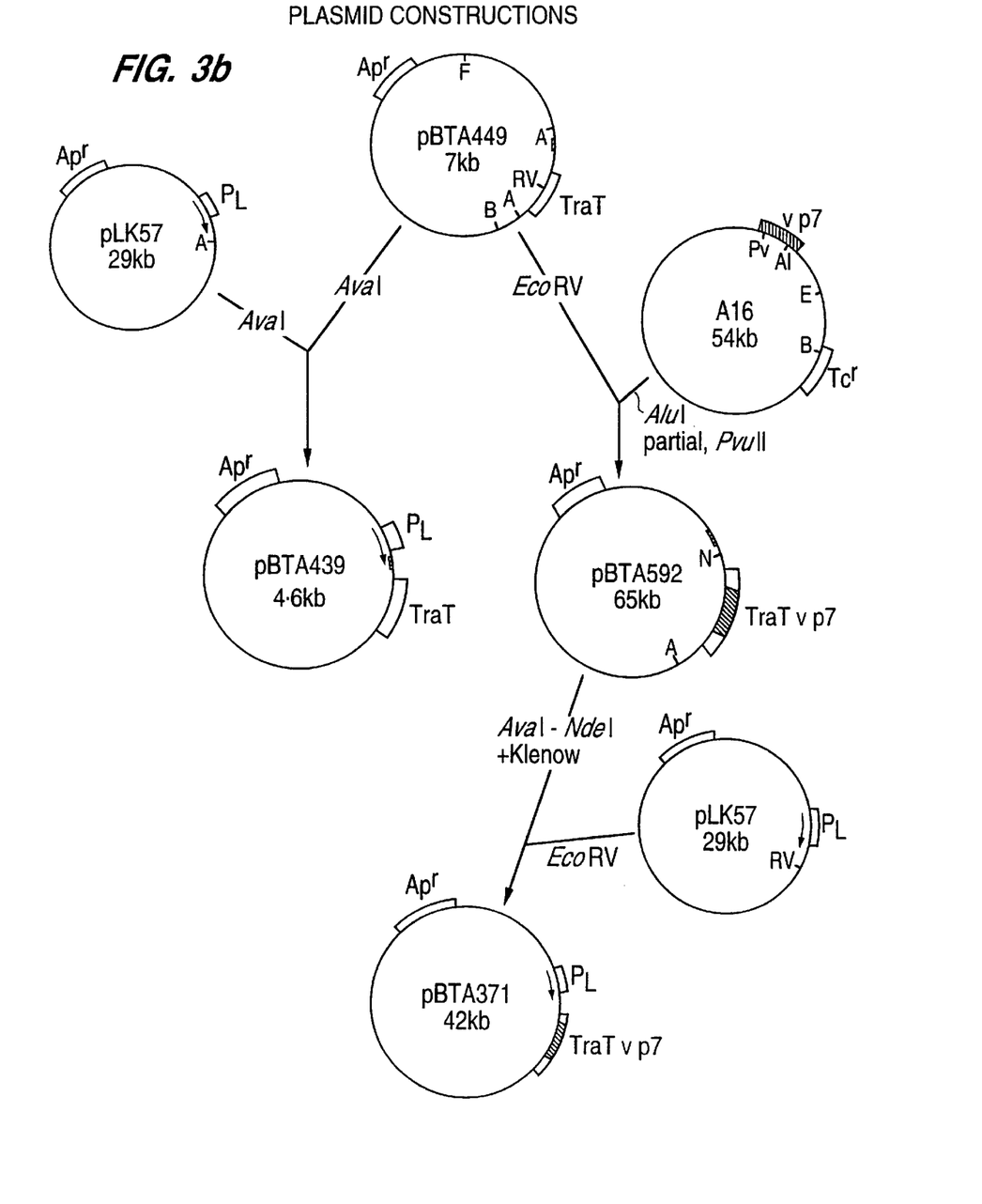
FIG. 3b shows construction of the plasmids pBTA439 and pBTA371.
Figure 4:
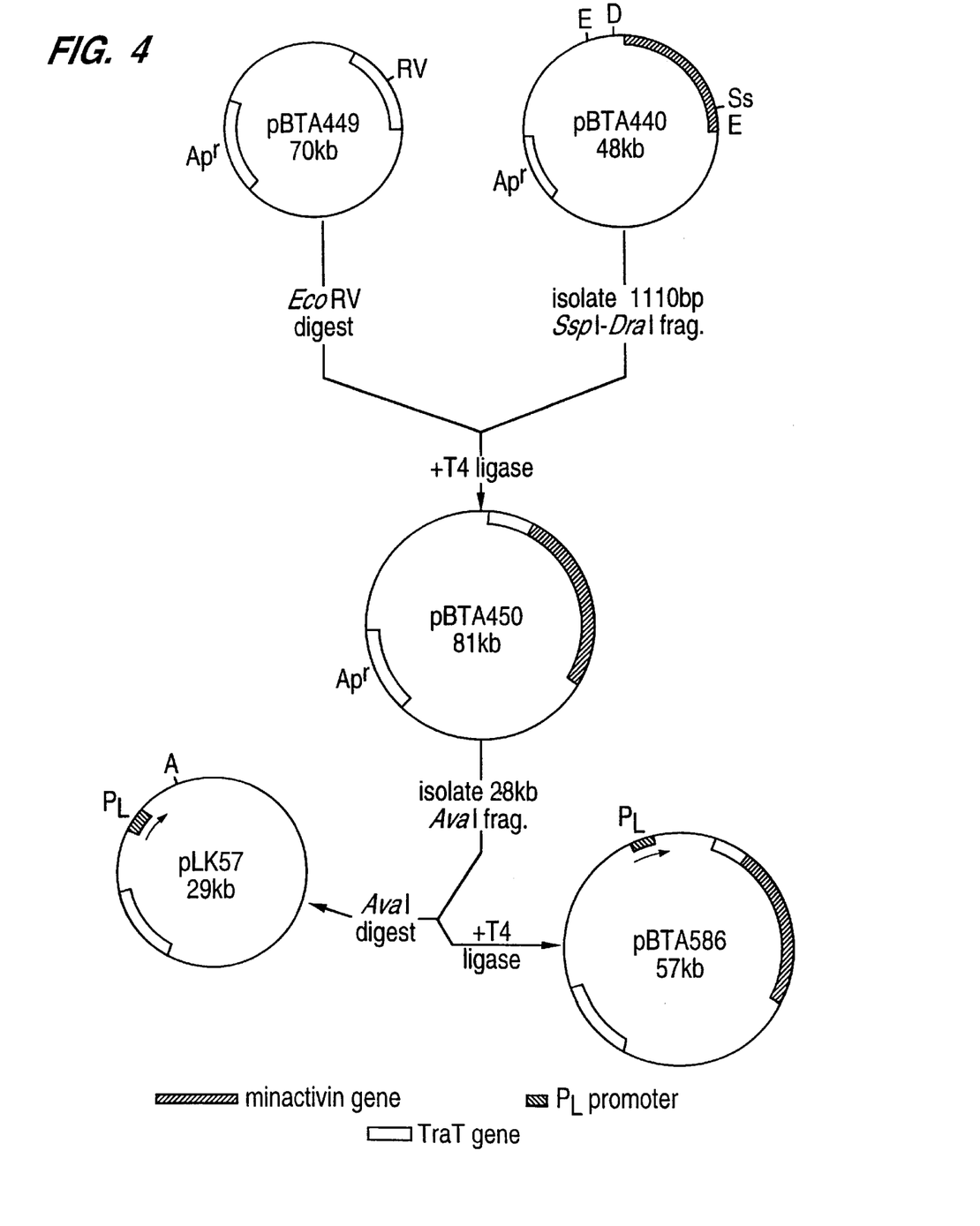
FIG. 4 shows the construction of the plasmids pBTA450 and pBTA586.

An AluI PvuII restriction fragment of the rotavirus NCDV VP7 gene was cloned into the EcoRV site of plasmid pBTA449 and subsequently overexpressed with the $P_L$ promoter (pBTA371, FIG. 3b). For expression the plasmid pBTA371 was used to transform E. coli K-12 strain N4830 (Joyce et al, PNAS 80, 1830–1834 1983) which contains the thermolabile cI repressor of Lambda. Cells transformed with pBTA371 were grown overnight in MEB medium (Mott et al PNAS 82, 88–92 1985) with 100 ug/ml ampicillin at 30° C. Cells were diluted in MEB medium, grown at 30° C. to an $OD_{600}$ of 1.0 when prewarmed (65°) MEB medium was added in equal volume to equilibrate the temperature to 42° C. Following 4 hours of growth at 42° C. the cells were harvested and examined for induction of the TraT-VP7 hybrid protein. In E. coli N4830 high level expression of the TraT-VP7 protein complex (10–15% total cell protein or greater than 500,000 copies per cell) was observed. A significant proportion of this complex was present in the outer membrane fraction.

In another example a method of producing a protein that is a hybrid of part of the TraT protein coding sequence and all or part of a eukaryotic protein coding sequence, minactivin, follows.

As shown in FIG. 4a the plasmid pBTA440 was digested with SspI and DraI and a 1110 bp fragment was isolated from an agarose gel. This fragment was ligated to the vector pBTA449 digested with EcoRV creating pBTA450. pBTA450 was then digested with AvaI and a purified 2800 bp fragment ligated to the plasmid pLK57 digested with AvaI to create plasmid pBTA586. This places part of the minactivin coding sequence under the control of the lambda $P_L$ promoter and fused to the coding sequence of the first 80 amino acids of TraT gene, the first 20 of which constitutes a signal sequence that results in the hybrid appearing in the outer membrane of E. coli. This signal sequence is cleaved off during transport to the outer membrane, which is the normal location of the TraT protein.

When plasmid pBTA586 is transformed into an appropriate host, such as N4830, and induced with temperature shift as described above, the TraT-minactivin hybrid protein appears in the outer membrance fraction.

EXAMPLE 8
Oral feeding of strains expressing TraT in the outer membrane

Female C57B1/65 mice (20–25 g) were fed $10^9$–$10^{10}$ bacteria (E. coli or a galE⁻ mutant of S. typhimurium) expressing TraT in their outer membranes. Controls received the same strains without the TraT protein. After 1 week mice were bled and the anti-TraT titres measured as outlined previously.

Results are expressed in Table 4 as reciprocal antibody titre and represent the average of 10 mice.

TABLE 4

Antibody Response to Orally Administered Whole Bacteria

| Strain | TraT | Anti TraT | | Anti OmpA | |
|---|---|---|---|---|---|
| | | Serum | Intestine | Serum | Intestine |
| E. coli | – | 3 | 5.2 | 14 | 2 |
| | + | 350 | 15 | 110 | 2 |
| Salmonella | – | 12 | 2 | ND | ND |
| | + | 650 | 6 | ND | ND |

INDUSTRIAL APPLICATION

The current invention is of use in the preparation of vaccines for use in humans, pets and meat animals, and in general for potentiating the response to an antigen on oral, enteral or parenteral administration.

We claim:

1. The recombinant DNA molecule pBTA439.

2. An isolated DNA segment encoding a fusion protein, wherein said fusion protein comprises an immunogen and a carrier molecule, wherein said immunogen is selected from the group consisting of an antigen and a hapten, and wherein said carrier molecule comprises the first 60 amino acids following the signal sequence of an E. coli TraT protein, and wherein the carrier molecule causes enhancement of the immune response of a host to the immunogen when the complex is administered to the host, regardless of whether the complex is administered parenterally, enterally or orally.

3. An isolated DNA segment according to claim 2, further comprising a DNA sequence encoding a signal sequence that directs the fusion protein to the cell surface when expressed in *E. coli*.

4. An isolated DNA segment according to claim 2, wherein said signal sequence is a TraT signal sequence.

5. An isolated DNA segment according to claim 2, further comprising an expression control sequence operatively linked to the DNA sequence encoding said fusion protein.

6. An isolated DNA segment according to claim 5, wherein said expression control sequence is a promoter functional in *E. coli*.

7. An isolated DNA segment according to claim 4, wherein said promoter is the $P_L$ promoter of bacteriophage λ.

8. An isolated DNA segment according to claim 5, further comprising vector DNA.

9. An isolated DNA segment encoding a fusion protein, wherein said fusion protein comprises a minactivin protein and a carrier molecule, and wherein said carrier molecule comprises the first 60 amino acids following the signal sequence of an *E. coli* TraT protein, and wherein the carrier molecule causes enhancement of the immune response of a host to minactivin when the complex is administered to the host, regardless of whether the complex is administered parenterally, enterally or orally.

10. An isolated DNA segment encoding a fusion protein, wherein said fusion protein comprises the rotavirus capsid protein VP7 and a carrier molecule, wherein said immunogen is selected from the group consisting of an antigen and a hapten, and wherein said carrier molecule comprises the first 60 amino acids following the signal sequence of an *E. coli* TraT protein, and wherein the carrier molecule causes enhancement of the immune response of a host to the VP7 protein when the complex is administered to the host, regardless of whether the complex is administered parenterally, enterally or orally.

11. An isolated DNA segment according to claim 8, wherein the vector DNA is of plasmid, bacteriophage, viral or cosmid origin.

12. A process for the production of a recombinant DNA molecule comprising:

introducing into vector DNA a DNA segment according to claim 2.

13. A process according to claim 12 which process additionally comprises introducing an expression control sequence into the vector DNA.

14. An isolated transformed host comprising a host cell transformed with at least one recombinant DNA segment according to claim 2.

15. An isolated transformed host according to claim 14, wherein said host is *E. coli* or a Salmonella species.

16. An isolated transformed host having the designation ATCC 67331.

17. A process for the transformation of a host, comprising:

introducing into a host a recombinant DNA segment according to claim 2.

18. A method for preparing a fusion protein, comprising culturing a host cell according to claim 14, and isolating said fusion protein.

* * * * *